(12) United States Patent
Iwami

(10) Patent No.: US 10,726,285 B2
(45) Date of Patent: Jul. 28, 2020

(54) MEDICINE AUDIT APPARATUS, METHOD, AND PROGRAM

(71) Applicant: FUJIFILM Corporation, Tokyo (JP)

(72) Inventor: Kazuchika Iwami, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 33 days.

(21) Appl. No.: 16/165,111

(22) Filed: Oct. 19, 2018

(65) Prior Publication Data
US 2019/0050660 A1  Feb. 14, 2019

Related U.S. Application Data

(63) Continuation of application No. PCT/JP2017/014261, filed on Apr. 5, 2017.

(30) Foreign Application Priority Data

Apr. 22, 2016  (JP) .................................. 2016-086032

(51) Int. Cl.
*G06K 9/03* (2006.01)
*G01N 21/85* (2006.01)
(Continued)

(52) U.S. Cl.
CPC ............... *G06K 9/036* (2013.01); *A61J 3/00* (2013.01); *A61J 7/02* (2013.01); *G01N 21/85* (2013.01);
(Continued)

(58) Field of Classification Search
None
See application file for complete search history.

(56) References Cited

U.S. PATENT DOCUMENTS

| 5,475,429 A | 12/1995 | Kodama |
| 10,217,012 B2 | 2/2019 | Hasegawa |

(Continued)

FOREIGN PATENT DOCUMENTS

| JP | 05-075910 A | 3/1993 |
| JP | 2000-018920 A | 1/2000 |

(Continued)

OTHER PUBLICATIONS

Communication dated Aug. 13, 2019, issued by the Japan Patent Office in corresponding application No. 2016-086032.
(Continued)

*Primary Examiner* — Dakshesh D Parikh
(74) *Attorney, Agent, or Firm* — Sughrue Mion, PLLC

(57) ABSTRACT

Provided are a medicine audit apparatus, a medicine audit method, and a program capable of detecting a state where recognition of a medicine is impossible from a captured image obtained by imaging the medicine and urging a user to pay attention in the case of the state where the medicine recognition is impossible. The medicine audit apparatus 10 comprises a medicine recognition unit 54 that specifies a type of the medicine by recognizing the medicine from the captured image obtained by imaging the medicine, a quantitative value calculation unit 50 that calculates a quantitative value for quantifying a quality of the captured image related to success or failure of the medicine recognition by the medicine recognition unit 54, a comparison determination unit 51 that compares the quantitative value calculated by the quantitative value calculation unit 50 with the threshold value to determine whether the recognition of the medicine is possible, and a warning output unit 58 that issues a warning in a case where the medicine recognition is determined to be impossible by the comparison determination unit 51.

8 Claims, 10 Drawing Sheets

(51) Int. Cl.
| | |
|---|---|
| A61J 3/00 | (2006.01) |
| G06K 9/00 | (2006.01) |
| G06T 7/00 | (2017.01) |
| G16H 20/13 | (2018.01) |
| H04N 5/232 | (2006.01) |
| G01N 21/95 | (2006.01) |
| G06T 7/13 | (2017.01) |
| A61J 7/02 | (2006.01) |
| A61J 7/04 | (2006.01) |
| G06K 9/20 | (2006.01) |

(52) U.S. Cl.
CPC ........... *G01N 21/9508* (2013.01); *G06K 9/00* (2013.01); *G06T 7/0002* (2013.01); *G06T 7/0012* (2013.01); *G06T 7/13* (2017.01); *G16H 20/13* (2018.01); *H04N 5/23229* (2013.01); *A61J 7/0454* (2015.05); *G06K 9/2036* (2013.01); *G06K 2209/01* (2013.01); *G06K 2209/19* (2013.01); *G06T 2207/20056* (2013.01); *G06T 2207/30168* (2013.01); *H04N 5/232* (2013.01)

(56) References Cited

U.S. PATENT DOCUMENTS

| | | |
|---|---|---|
| 2006/0146174 A1 | 7/2006 | Hagino |
| 2014/0119644 A1 | 5/2014 | Zheng et al. |
| 2015/0065803 A1* | 3/2015 | Douglas ............. A61B 1/00009 600/200 |
| 2016/0210524 A1* | 7/2016 | Hasegawa ............. G01N 21/85 |

FOREIGN PATENT DOCUMENTS

| | | | |
|---|---|---|---|
| JP | 2000-180380 A | 6/2000 | |
| JP | 2004-297751 A | 10/2004 | |
| JP | 2011-220828 A | 11/2011 | |
| JP | 2015-068765 A | 4/2015 | |
| JP | WO2015/046044 A1 * | 4/2015 | ............. G01N 21/85 |
| JP | 2015-535108 A | 12/2015 | |
| WO | 2015046044 A1 | 4/2015 | |

OTHER PUBLICATIONS

Communication dated Mar. 19, 2019 from the European Patent Office in application No. 17785800.8.
Vincent, O.R., et al., "A Descriptive Algorithm for Sobel Image Edge Detection", Proceedings of Informing Science & IT Education Conference (InSITE), 2009, pp. 97-107 (11 pages), XP055562234.
International Search Report of PCT/JP2017/014261 dated Jun. 27, 2017.
International Preliminary Report on Patentability with English Translation of the Written Opinion of PCT/JP2017/014261 dated Aug. 29, 2018.
Written Opinion of PCT/JP2017/014261 dated Jun. 27, 2017.

* cited by examiner

FIG. 9

| C | 0.0 | 0.1 | 0.2 | 0.3 | 0.4 | 0.5 | 0.6 | 0.7 | 0.8 | 0.9 | 1.0 |
|---|---|---|---|---|---|---|---|---|---|---|---|
| MEDICINE OUTLINE EXTRACTION PROPRIETY | A | A | A | A | A | A | A | A | A | A | A |
| T | 1.60 | 1.56 | 1.53 | 1.50 | 1.46 | 1.43 | 1.40 | 1.37 | 1.34 | 1.32 | 1.29 |
| C | — | 1.1 | 1.2 | 1.3 | 1.4 | 1.5 | 1.6 | 1.7 | 1.8 | 1.9 | 2.0 |
| MEDICINE OUTLINE EXTRACTION PROPRIETY | — | A | A | A | A | D | D | D | D | D | D |
| T | — | 1.26 | 1.24 | 1.21 | 1.19 | 1.17 | 1.15 | 1.12 | 1.10 | 1.08 | 1.06 |

MEDICINE AUDIT APPARATUS, METHOD, AND PROGRAM

CROSS-REFERENCE TO RELATED APPLICATIONS

The present application is a Continuation of PCT International Application No. PCT/JP2017/014261 filed on Apr. 5, 2017 claiming priority under 35 U.S.C. § 119(a) to Japanese Patent Application No. 2016-086032 filed on Apr. 22, 2016. Each of the above applications is hereby expressly incorporated by reference, in their entirety, into the present application.

BACKGROUND OF THE INVENTION

1. Field of the Invention

The present invention relates to a medicine audit apparatus, a medicine audit method, and a program, and particularly to a medicine audit support technique that distinguishes types of medicines from an image obtained by imaging the medicines.

2. Description of the Related Art

In recent years, in a hospital or the like, for example, in a case where a plurality of types of medicines having different dose timings are prescribed to a patient, a one-packaging dispensing for packaging the plurality of types of medicines dosed at one time in one packaging bag is performed in many cases. Examples of the dose timing are after breakfast, after lunch, and after dinner. In the one-packaging dispensing, a pharmacist picks and sets each medicine according to a prescription on a tray of a packaging machine for each dose at one time, and then the packaging machine automatically packages the medicines in the tray in each packaging bag. The tray of the packaging machine is also referred to as a tablet case.

In such one-packaging dispensing, since there is a case where the pharmacist manually performs the picking of the medicines and the setting on the packaging tray, there is a possibility that medicines having different types or numbers from an instruction of the prescription are incorrectly packaged. Thus, in order to determine whether the packaged medicines match the prescription, automatic recognition of the types or the number of the medicines is performed before or after the packaging in the packaging bag.

A medicine recognition apparatus disclosed in JP2015-068765A includes an illumination unit capable of illuminating a medicine with an engraved character from a plurality of illumination directions surrounding the periphery of the medicine, an illumination control unit that sequentially switches the illumination direction in which the illumination unit illuminates the medicine, an imaging unit that images the medicine illuminated by the illumination unit and repeatedly images the medicine every time the illumination direction is switched, a feature image extraction unit that extracts a feature image corresponding to a shadow of each engraved character from a captured image for each illumination direction acquired by the imaging unit, a feature image integration unit that integrates the feature image for each illumination direction extracted by the feature image extraction unit to generate an integration image, and a recognition unit that recognizes the engraved character included in the integration image generated by the feature image integration unit to recognize a type of the medicine based on a recognition result of the engraved character. A term of the medicine recognition apparatus is understood to be a term corresponding to a medicine audit apparatus of the specification.

SUMMARY OF THE INVENTION

In the medicine recognition apparatus disclosed in JP2015-068765A, in a case where the engraved character cannot be recognized, it is determined that the recognition of the medicine fails, and the determination result is output to a display unit (paragraph 0053 of JP2015-068765A). However, JP2015-068765A does not specifically disclose a detection method in the case where the engraved character cannot be recognized.

In order to make work of a medicine audit even more efficient, it is desirable to detect a problem in the case where the recognition of the medicine fails and to inform a user of the problem. The problem is not limited to the case of recognizing the engraved character and is a problem common to a case where a printed character printed on a medicine surface is recognized. The problem is not limited to the medicine audit in the one-packaging dispensing and is a problem common to the medicine audit using processing of recognizing the type of the medicine from the image obtained by imaging the medicine.

The present invention is made in view of such circumstances, and a purpose of the present invention is to provide a new detection technique for detecting a state where recognition of a medicine from an image obtained by imaging a medicine is impossible and to provide a medicine audit apparatus, a medicine audit method, and a program capable of urging a user to pay attention in the case of the state where the medicine recognition is impossible.

A medicine audit apparatus according to a first embodiment of the disclosure comprises an image acquisition unit that acquires a captured image obtained by imaging a medicine, a medicine recognition unit that specifies a type of the medicine by recognizing the medicine from the captured image, a quantitative value calculation unit that calculates a quantitative value for quantifying a quality of the captured image related to success or failure of the medicine recognition by the medicine recognition unit, a storage unit that stores a threshold value of a quantitative value that is a determination criterion whether the medicine recognition by the medicine recognition unit is possible, a comparison determination unit that compares the quantitative value calculated by the quantitative value calculation unit with the threshold value to determine whether the recognition of the medicine by the medicine recognition unit is possible, and a warning output unit that issues a warning in a case where the medicine recognition of the medicine recognition unit is determined to be impossible by the comparison determination unit.

There is a problem of the quality of the captured image as one reason why the recognition of the medicine from the captured image is impossible. In the medicine audit apparatus according to the first embodiment, a relationship between the quantitative value for quantitatively evaluating the quality of the captured image and success or failure of the medicine recognition is known in advance, and the threshold value of the quantitative value at which the medicine recognition is impossible is decided. According to the first embodiment, it is possible to detect a state of the quality in which the medicine recognition is impossible by comparing the quantitative value calculated from the captured image with the threshold value. In a case where the medicine recognition is determined to be impossible, it is possible to urge a user to pay attention by issuing the warning.

As a second embodiment, in the medicine audit apparatus according to the first embodiment, the quality of the captured image related to success or failure of the medicine recognition by the medicine recognition unit may include sharpness of the captured image.

As a third embodiment, in the medicine audit apparatus according to the first embodiment or the second embodiment, the medicine recognition unit may include an edge detection unit that detects an edge of the medicine from the captured image, and an engraved mark recognition unit that recognizes an engraved mark assigned on the medicine extracted based on information on the edge detected by the edge detection unit from the captured image.

As a fourth embodiment, in the medicine audit apparatus according to the third embodiment, the quantitative value may be a quantitative value for quantifying the quality of the captured image related to success or failure of the edge detection by the edge detection unit, the threshold value may be a threshold value of a quantitative value that is a determination criterion whether the edge detection by the edge detection unit is possible, the determination whether the recognition of the medicine by the medicine recognition unit is possible performed by the comparison determination unit may be a determination whether the edge detection by the edge detection unit is possible, and in a case where the edge detection by the edge detection unit is determined to be impossible by the comparison determination unit, the warning output unit may issue the warning.

As a fifth embodiment, in the medicine audit apparatus according to any one embodiment of the first embodiment to the fourth embodiment, the quantitative value calculation unit may calculate the quantitative value defined using a ratio between a sum of absolute values of spatial frequency spectra of higher frequencies than one cycle/mm and a sum of absolute values of spatial frequency spectra of lower frequencies than one cycle/mm in the spatial frequency spectra obtained by performing processing of two-dimensional Fourier transform on the captured image in a radial direction.

As a sixth embodiment, in the medicine audit apparatus according to any one embodiment of the first embodiment to the fifth embodiment, in a case where the quantitative value calculated by the quantitative value calculation unit is less than the threshold value, the warning output unit may output the warning.

As a seventh embodiment, in the medicine audit apparatus according to any one embodiment of the first embodiment to the sixth embodiment, the warning output unit may include a display unit that displays information on the warning.

As an eighth embodiment, in the medicine audit apparatus according to any one embodiment of the first embodiment to the seventh embodiment, a camera that images the medicine may be further comprised, and the image acquisition unit may acquire a captured image imaged by the camera.

As a ninth embodiment, in the medicine audit apparatus according to any one embodiment of the first embodiment to the eighth embodiment, the captured image may be an image obtained by imaging one-packaging medicines for one package in which a plurality of types of medicines are accommodated in a packaging bag.

A medicine audit method according to a tenth embodiment includes an image acquisition step of acquiring a captured image obtained by imaging a medicine, a medicine recognition step of specifying a type of the medicine by recognizing the medicine from the captured image, a quantitative value calculation step of calculating a quantitative value for quantifying a quality of the captured image related to success or failure of the medicine recognition by the medicine recognition step, a comparison determination step of storing a threshold value of a quantitative value that is a determination criterion whether the medicine recognition by the medicine recognition step is possible, and comparing the quantitative value calculated by the quantitative value calculation step with the threshold value to determine whether the recognition of the medicine by the medicine recognition step is possible, and a warning output step of issuing a warning in a case where the medicine recognition of the medicine recognition step is determined to be impossible in the comparison determination step.

In the tenth embodiment, it is possible to combine the same items as the items specified in the second embodiment to the ninth embodiment as appropriate. In the case, it is possible to grasp means or the component of a function to be specified by the medicine audit apparatus as the component of processing or step of an operation corresponding to the specified means or component.

A program according to an eleventh embodiment is a program causing a computer to execute an image acquisition step of acquiring a captured image obtained by imaging a medicine, a medicine recognition step of specifying a type of the medicine by recognizing the medicine from the captured image, a quantitative value calculation step of calculating a quantitative value for quantifying a quality of the captured image related to success or failure of the medicine recognition by the medicine recognition step, a comparison determination step of storing a threshold value of a quantitative value that is a determination criterion whether the medicine recognition by the medicine recognition step is possible, and comparing the quantitative value calculated by the quantitative value calculation step with the threshold value to determine whether the recognition of the medicine by the medicine recognition step is possible, and a warning output step of issuing a warning in a case where the medicine recognition of the medicine recognition step is determined to be impossible in the comparison determination step.

In the eleventh embodiment, it is possible to combine the same items as the items specified in the second embodiment to the ninth embodiment as appropriate. In the case, it is possible to grasp means or the component of a function to be specified by the medicine audit apparatus as the program component realizing functions of processing or step of an operation corresponding to the specified means or component.

According to the present invention, it is possible to detect the state where the recognition of the medicine from the image obtained by imaging the medicine is impossible. According to the present invention, in the case where the state where the medicine recognition is impossible is detected, it is possible to urge the user to pay attention.

BRIEF DESCRIPTION OF THE DRAWINGS

FIG. 9 is a table summarizing predetermined values of a parameter C using simulation, propriety results of outline extractions of the medicines, and values of a quantitative value T calculated under each condition.

DESCRIPTION OF THE PREFERRED EMBODIMENTS

Hereinafter, an embodiment of the present invention will be described according to accompanying drawings.

[Configuration of Medicine Audit Apparatus According to Embodiment]

Figure 1:
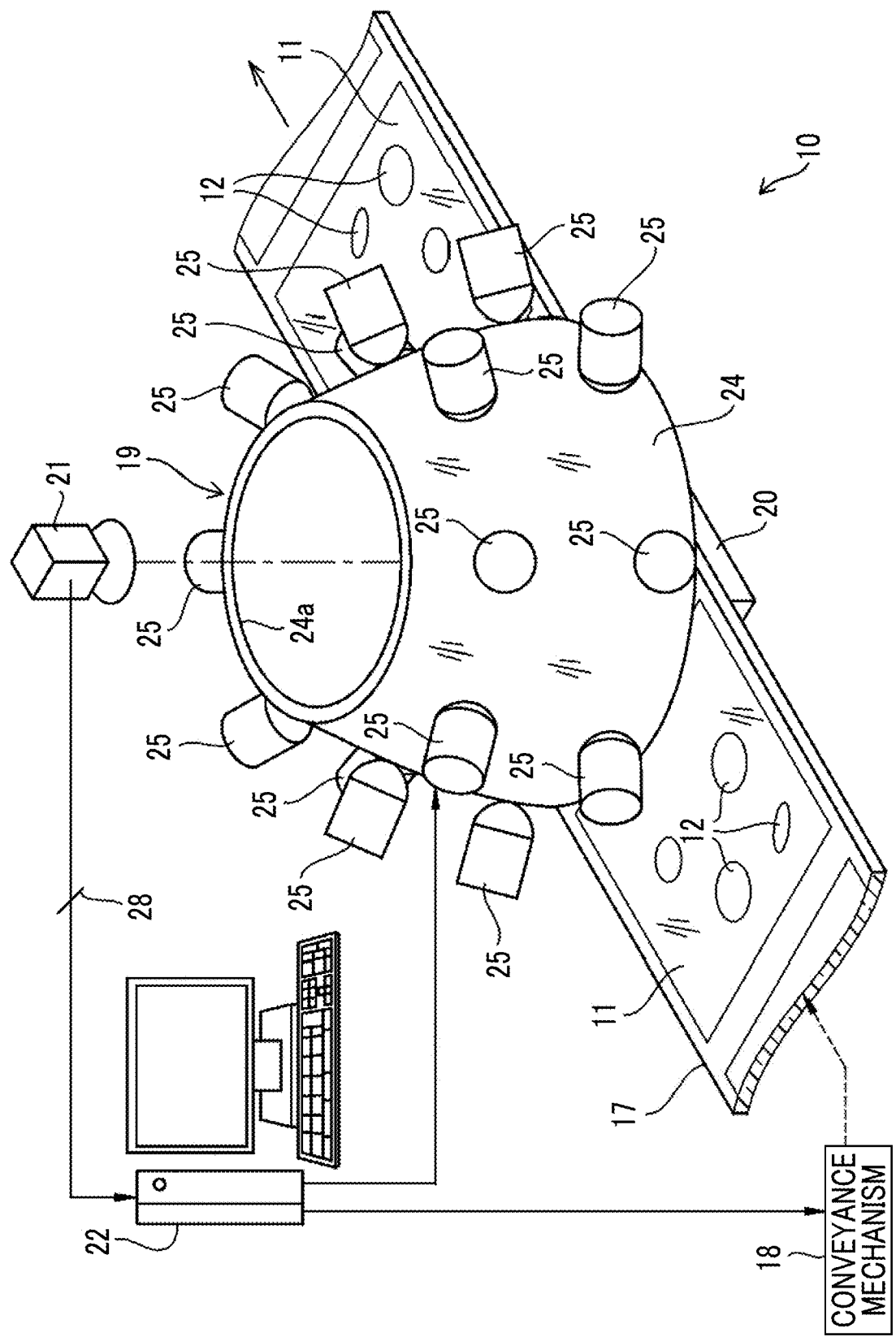
FIG. 1 is a perspective view of a medicine audit apparatus according to an embodiment.

FIG. 1 is a perspective view of a medicine audit apparatus 10 according to the embodiment. The medicine audit apparatus 10 recognizes a type of medicine 12 packaged in a packaging bag 11 and audits whether the medicine 12 in the packaging bag 11 matches a prescription not shown. The packaging bag 11 is a transparent or semitransparent medicine accommodation bag. The medicine 12 herein is a solid medicine, for example, a tablet or a capsule. An engraved character or a printed character not shown is assigned on a surface of the medicine 12. In the specification, identification information by the engraved character assigned on the medicine surface or the printed character printed on the medicine surface is referred to as "engraved mark". A plurality of medicines 12 are accommodated in the packaging bag 11. The plurality of medicines 12 accommodated in one packaging bag 11 may include different types of medicines or the same types of medicines. The medicines 12 packaged in the packaging bag 11 are referred to as one-packaging medicines.

The medicine audit apparatus 10 comprises a tray 17, a conveyance mechanism 18, a projector 19, a backlight 20, a camera 21, and an information processing apparatus 22. A series of packaging bags 11 in which the medicines 12 for one package are respectively packaged by a packaging apparatus not shown is placed on the tray 17. The tray 17 is formed by a transparent or semitransparent material, and illumination light irradiated from the backlight 20 passes through the tray 17. The transparent or semitransparent material is synonymous with a material having optical transparency.

The conveyance mechanism 18 intermittently conveys the tray 17 along the longitudinal direction of the series of packaging bags 11 continued in a belt shape. The conveyance mechanism 18 includes a power source such as a motor not shown. Hereinafter, the longitudinal direction of the series of packaging bags 11 is simply referred to as "longitudinal direction". The projector 19, the backlight 20, and the camera 21 are respectively installed at fixed positions, and the tray 17 is conveyed by the conveyance mechanism 18 to relatively move the series of packaging bags 11 in the longitudinal direction with respect to the projector 19, the backlight 20, and the camera 21. The projector 19, the backlight 20, and the camera 21 may be conveyed in the longitudinal direction of the packaging bag 11 instead of conveying the tray 17.

The projector 19 is disposed on an upper surface side of the tray 17 and sequentially illuminates the packaging bag 11 intermittently conveyed by the conveyance mechanism 18 for each one-package. The upper surface of the tray 17 is a surface on a placement surface side that is in contact with the packaging bag 11 on the tray 17. In the description of FIG. 1, a surface facing an upper direction in the drawing is the upper surface of the tray 17. A surface on a side opposite to the backlight 20 of the tray 17 is referred to as a lower surface of the tray 17. In the embodiment, a direction away from the tray 17 on the upper surface side of the tray 17 is the upper direction, and a direction away from the tray 17 on a lower surface side of the tray 17 is a lower direction.

Figure 2:
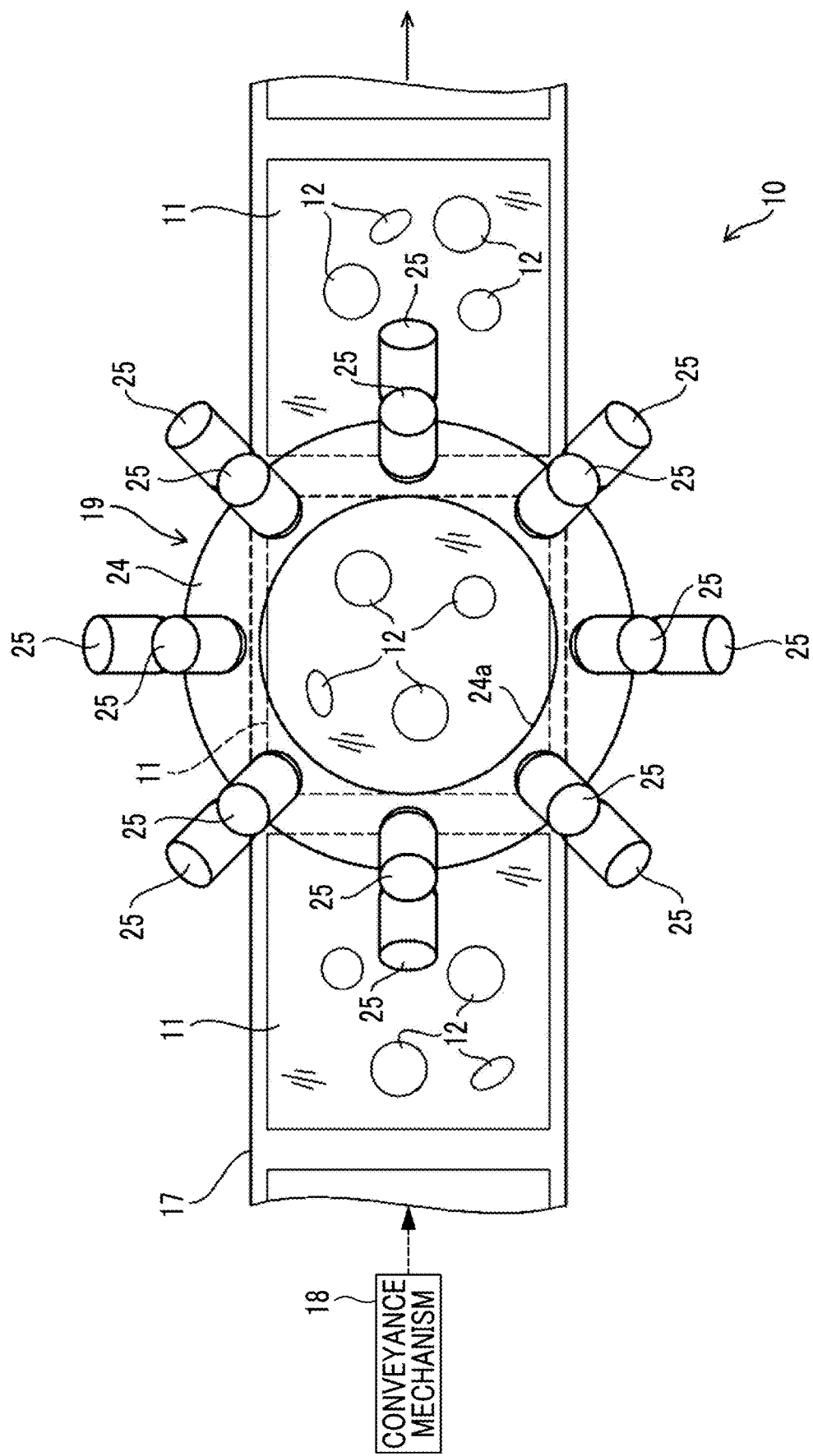
FIG. 2 is a top view of a projector.

The projector 19 is configured to include a light source holding unit 24 and a plurality of point light sources 25. The light source holding unit 24 is a holding member that holds the plurality of point light sources 25. The light source holding unit 24 is formed by the material having the optical transparency. The light source holding unit 24 is formed in a substantial dome shape covering the packaging bag 11 for one package. In a ceiling portion of the light source holding unit 24, an opening window 24a exposing the inside of the light source holding unit 24 is formed. Accordingly, it is possible to confirm the medicine 12 in the light source holding unit 24 through the opening window 24a from an upper side of the light source holding unit 24. The medicine 12 in the light source holding unit 24 refers to the medicine 12 packaged in the packaging bag 11 located in the light source holding unit 24. FIG. 2 is a top view of the projector 19.

For example, a light emitting diode (LED) light source or the like is used as a point light source 25. Eight point light sources 25 are attached at regular spacing along respective circumferential directions of a lower stage part and an upper stage part on an outside surface of the light source holding unit 24. These 16 point light sources 25 irradiate the illumination light toward the medicine 12 in the light source holding unit 24.

The projector 19 can illuminate the medicine 12 in the light source holding unit 24 from a plurality of illumination directions by each point light source 25. The projector 19 can switch the illumination direction that illuminates the medicine 12 in the light source holding unit 24 by individually controlling on and off of the 16 point light sources.

As shown in FIG. 1, the backlight 20 is disposed at a position on the lower surface side of the tray 17 and a position opposite to the projector 19 across the tray 17. The backlight 20 illuminates the medicine 12 in the light source holding unit 24 from behind through the tray 17.

The camera 21 is an imaging apparatus that mounts an imaging device (not shown) represented by a charge-coupled device (CCD) sensor or a complementary metal-oxide semiconductor device (CMOS) sensor. It is preferable to use a color imaging device comprising a color filter as the imaging device. The camera 21 includes an optical system such as an imaging lens not shown. The camera 21 may comprise a signal processing circuit such as an analog front end circuit that processes an image signal output from the imaging device. The camera 21 converts an image of an object and generates the image signal corresponding to the object. The image signal may be an analog signal or a digital signal. In the example, it is assumed that the image signal having a digital format is output from the camera 21. The image signal having the digital format is referred to as image data.

The camera 21 is disposed on the upper side of the opening window 24*a*. The camera 21 images the medicine 12 in the light source holding unit 24 through the opening window 24*a* to generate image data 28. The camera 21 outputs the image data 28 generated by the imaging to the information processing apparatus 22. The image data 28 corresponds to one embodiment of a captured image.

In a first embodiment shown in FIG. 1, the surface on one side that is the upper surface side of the packaging bag 11 placed on the tray 17 is imaged by the camera 21 to acquire the captured image imaged from the upper surface side. However, in addition to such configuration, it is preferable to acquire a captured image imaged from the lower surface side of the packaging bag 11 by employing a configuration of disposing the projector and the camera not shown also on the lower surface side of the tray 17.

Figure 3:
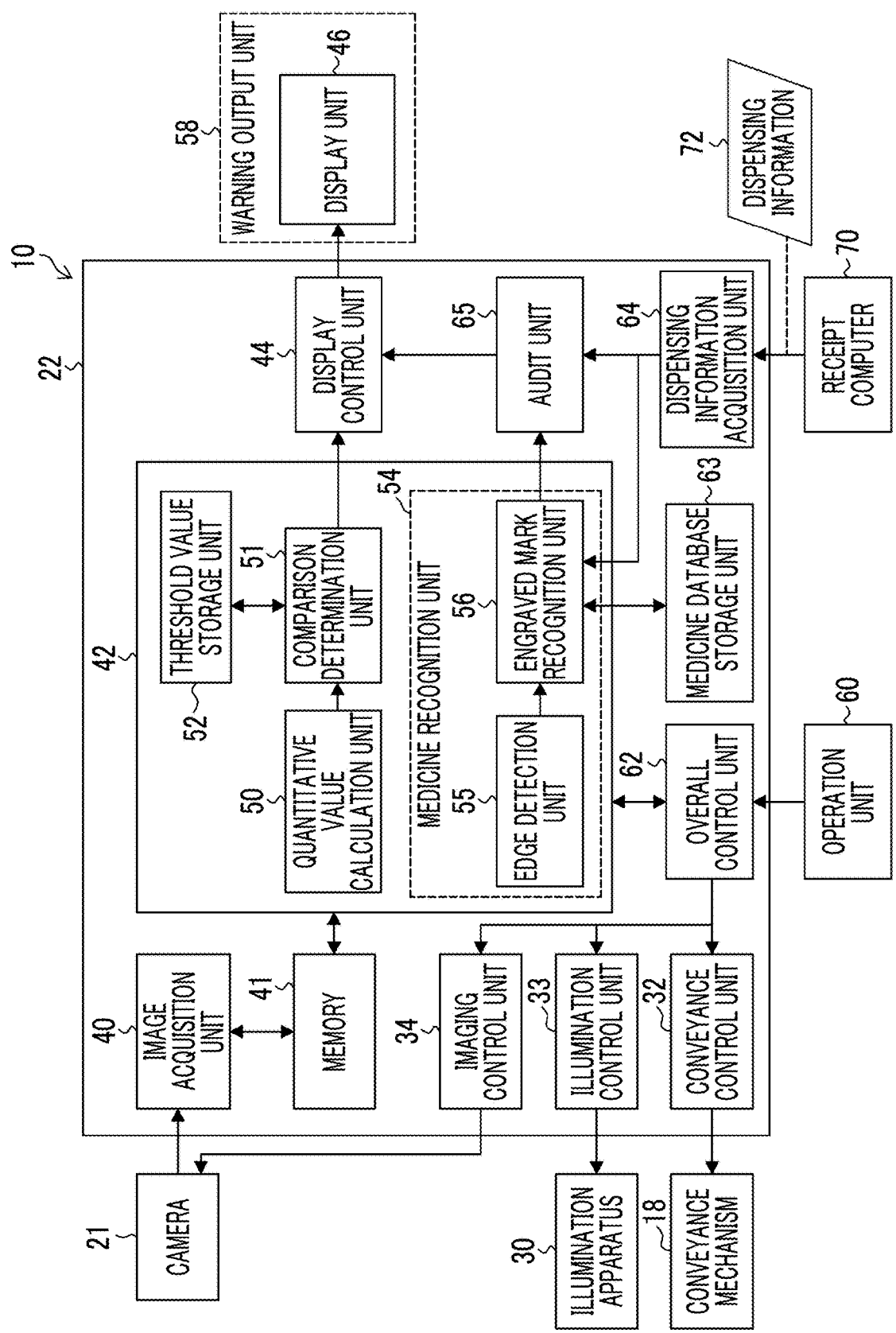
FIG. 3 is a functional block diagram of the medicine audit apparatus according to the embodiment.

FIG. 3 is a functional block diagram of the medicine audit apparatus 10. For example, a personal computer may be used as the information processing apparatus 22. The information processing apparatus 22 is respectively connected to the conveyance mechanism 18, an illumination apparatus 30, and the camera 21. The illumination apparatus 30 refers to the projector 19 and the backlight 20 described in FIG. 1. The "connection" is not limited to a wired connection and may be a wireless connection. A state where a signal transfer is possible is included in the concept of "connection". The information processing apparatus 22 of the example functions as a control apparatus of the medicine audit apparatus 10 and as a calculation apparatus that performs image processing and various other pieces of calculation processing.

The information processing apparatus 22 comprises a conveyance control unit 32, an illumination control unit 33, and an imaging control unit 34, and controls operations of the conveyance mechanism 18, the illumination apparatus 30, and the camera 21. The information processing apparatus 22 comprises an image acquisition unit 40, a memory 41, an image processing unit 42, a display control unit 44, and a display unit 46. The image processing unit 42 includes a quantitative value calculation unit 50, a comparison determination unit 51, a threshold value storage unit 52, and a medicine recognition unit 54. The medicine recognition unit 54 is configured to have an edge detection unit 55 and an engraved mark recognition unit 56. The information processing apparatus 22 further comprises an operation unit 60, an overall control unit 62, a medicine database storage unit 63, a dispensing information acquisition unit 64, and an audit unit 65.

It is possible to realize functions of each unit of the information processing apparatus 22 by combining hardware and software of a computer. The "software" is synonymous with "program". It is possible to realize a part or all processing functions in the information processing apparatus 22 by an integrated circuit or the like.

The conveyance control unit 32 controls driving of the conveyance mechanism 18 based on a command from the overall control unit 62. The illumination control unit 33 controls an emission of the illumination light by the illumination apparatus 30 based on the command from the overall control unit 62. The illumination control unit 33 may control light emission of the point light source 25 and the backlight 20 of the projector 19 described in FIG. 1 and may change an illumination condition that illuminates the medicine 12 in the light source holding unit 24.

The imaging control unit 34 shown in FIG. 3 controls an imaging operation by the camera 21 based on the command from the overall control unit 62. The imaging control unit 34 causes the camera 21 to execute the imaging every time the intermittent conveyance by the conveyance mechanism 18 stops, that is, for each packaging bag 11 for one package. In a case where a plurality of times of imaging are performed while the illumination condition is changed for the same packaging bag 11, the imaging control unit 34 causes the camera 21 to execute the imaging every time the switching of the illumination condition is executed.

The image acquisition unit 40 is an interface unit that acquires the captured image imaged by the camera 21. The image acquisition unit 40 can be configured by a data input terminal that captures the image data output from the camera 21. A wired or wireless communication interface unit may be employed as the image acquisition unit 40. The captured image acquired through the image acquisition unit 40 is stored in the memory 41.

The memory 41 functions as a storage unit that stores the captured image acquired through the image acquisition unit 40. The memory 41 may function as the storage unit that stores various control programs executed by the overall control unit 62 and various pieces of data necessary for the control, and may function as a work memory in a case where various calculations of the image processing unit 42 are performed.

The image processing unit 42 analyzes the captured image acquired through the image acquisition unit 40 to recognize the type of the medicine 12. The image processing unit 42 analyzes the captured image to perform processing of detecting a state where medicine recognition by the medicine recognition unit 54 is impossible. The image processing unit 42 may include a processing unit (not shown) that performs one or a plurality of pieces of processing of noise removal processing, color conversion processing, image rotation processing, trimming processing, or composite processing.

The quantitative value calculation unit 50 calculates a quantitative value for quantifying a quality of the captured image related to success or failure of the medicine recognition by the medicine recognition unit 54. The quantitative value calculation unit 50 according to the embodiment calculates a quantitative value for quantifying the sharpness of the captured image related to success or failure of edge detection by the edge detection unit 55. The sharpness of the captured image is an example of the quality of the captured image related to success or failure of the medicine recognition by the medicine recognition unit 54.

The quantitative value calculation unit 50 calculates a quantitative value defined using a ratio between a sum of absolute values of spatial frequency spectra of higher frequencies than one [cycle/mm] and a sum of absolute values of spatial frequency spectra of lower frequencies than one [cycle/mm] in the spatial frequency spectra of a two-dimensional fast Fourier transform image obtained by performing processing of two-dimensional fast Fourier transform on the captured image in a radial direction.

The threshold value storage unit 52 is the storage unit that stores a threshold value of the quantitative value that is a determination criterion whether the medicine recognition by the medicine recognition unit 54 is possible. As a deciding method of the threshold value, a relationship between the quantitative value and success or failure of the medicine recognition is checked based on, for example, simulation, and a condition of the quantitative value at which the medicine recognition is impossible is decided as the threshold value.

The comparison determination unit 51 acquires information of the threshold value from the threshold value storage unit 52. The comparison determination unit 51 compares the quantitative value calculated by the quantitative value calculation unit 50 with the threshold value to determine whether the medicine recognition by the medicine recognition unit 54 is possible. A method of the processing of detecting the state where the medicine recognition is impossible in the image processing unit 42 will be described below in detail including a specific example of the deciding method of the threshold value.

The medicine audit apparatus 10 comprises a warning output unit 58 that issues a warning in a case where the medicine recognition of the medicine recognition unit 54 by the comparison determination unit 51 is determined to be impossible. The warning output unit 58 includes the display unit 46. In the case where the state where the medicine recognition is impossible is determined by the comparison determination unit 51, warning information informing the state where the medicine recognition is impossible is displayed on the display unit 46 through the display control unit 44. The warning output unit 58 is configured to have a warning lamp, an apparatus that generates a warning sound, an apparatus that generates a sound, or a combination thereof as appropriate in addition to the display unit 46.

The medicine recognition unit 54 recognizes the medicine from the captured image to specify the type of the medicine. The edge detection unit 55 performs known edge detection processing on the captured image to extract an outline of the medicine in the captured image. For example, a method of Canny edge detection may be used as a method of the edge detection processing in the edge detection unit 55.

The engraved mark recognition unit 56 detects an outline of the engraved mark assigned on each medicine 12 from a medicine region extracted based on information on an edge detected by the edge detection unit 55 to recognize character information indicated by the engraved mark.

The medicine database storage unit 63 stores a medicine database that is an aggregate of medicine data in which medicine information including an appearance image of the medicine and information on the engraved mark is associated with each type of the medicine. The medicine recognition unit 54 can specify the type of the medicine from the engraved mark recognized by the engraved mark recognition unit 56 with reference to the medicine database.

The dispensing information acquisition unit 64 acquires dispensing information 72 from a receipt computer 70. The receipt computer 70 holds the dispensing information 72 based on a description on the prescription. In a case where the dispensing is performed, a pharmacist performs work of inputting the dispensing information 72 to the receipt computer 70 based on dispensing information described on the prescription. The dispensing information 72 includes the name and age of a patient, a medicine name, a quantity, usage, a dosage, and the like. The medicine name input to the receipt computer 70 is not limited to the medicine name described on the prescription and may be a medicine name of a follow-on drug having the same ingredient and the same medicinal effect as the described medicine.

In the packaging apparatus, the medicines 12 are respectively packaged in the series of packaging bags 11 according to the dispensing information 72 input to the receipt computer 70. The audit unit 65 can distinguish the types and the number of the medicines 12 required to be packaged in each packaging bag 11 based on the dispensing information 72 acquired from the dispensing information acquisition unit 64.

The engraved mark recognition unit 56 can acquire the information on the engraved mark assigned on each medicine described in the dispensing information 72 with reference to the medicine database based on the dispensing information 72. The engraved mark recognition unit 56 compares the information on the engraved mark obtained by referring to the medicine database from the dispensing information 72 with the outline of the engraved mark extracted from the captured image to recognize the engraved mark assigned on the medicine 12 included in the captured image. The medicine recognition unit 54 specifies the type of the medicine 12 corresponding to each engraved mark with reference to the medicine database based on a recognition result of the engraved mark. Accordingly, the type of the medicine 12 for one package is recognized. The medicine recognition unit 54 outputs the recognition result of the type of the medicine 12 for one package to the audit unit 65.

The audit unit 65 collates the recognition result of the type of the medicine 12 for one package input from the medicine recognition unit 54 with the type of the medicine for one package recorded in the dispensing information 72. Information on a collation result by the audit unit 65 is displayed on the display unit 46 through the display control unit 44.

The display control unit 44 performs a control for displaying various pieces of information on the display unit 46. The display control unit 44 performs processing of generating a signal for displaying on the display unit 46.

A display device by various display methods such as a liquid crystal display and an organic electro-luminescence (EL) display may be used as the display unit 46. Pieces of work such as an input of an instruction and setting to the information processing apparatus 22 by a user can be performed by using the operation unit 60 and the display unit 46. A combination of the display unit 46 and the operation unit 60 functions as a user interface of the medicine audit apparatus 10.

The operation unit 60 is means for the user such as the pharmacist to perform an operation to input the various pieces of information. Various input apparatuses such as a keyboard, a mouse, a touch panel, a trackball, or an operation button may be employed as the operation unit 60, and a combination thereof as appropriate also may be employed.

[Description of Audit Processing by Medicine Audit Apparatus 10]

Figure 4:
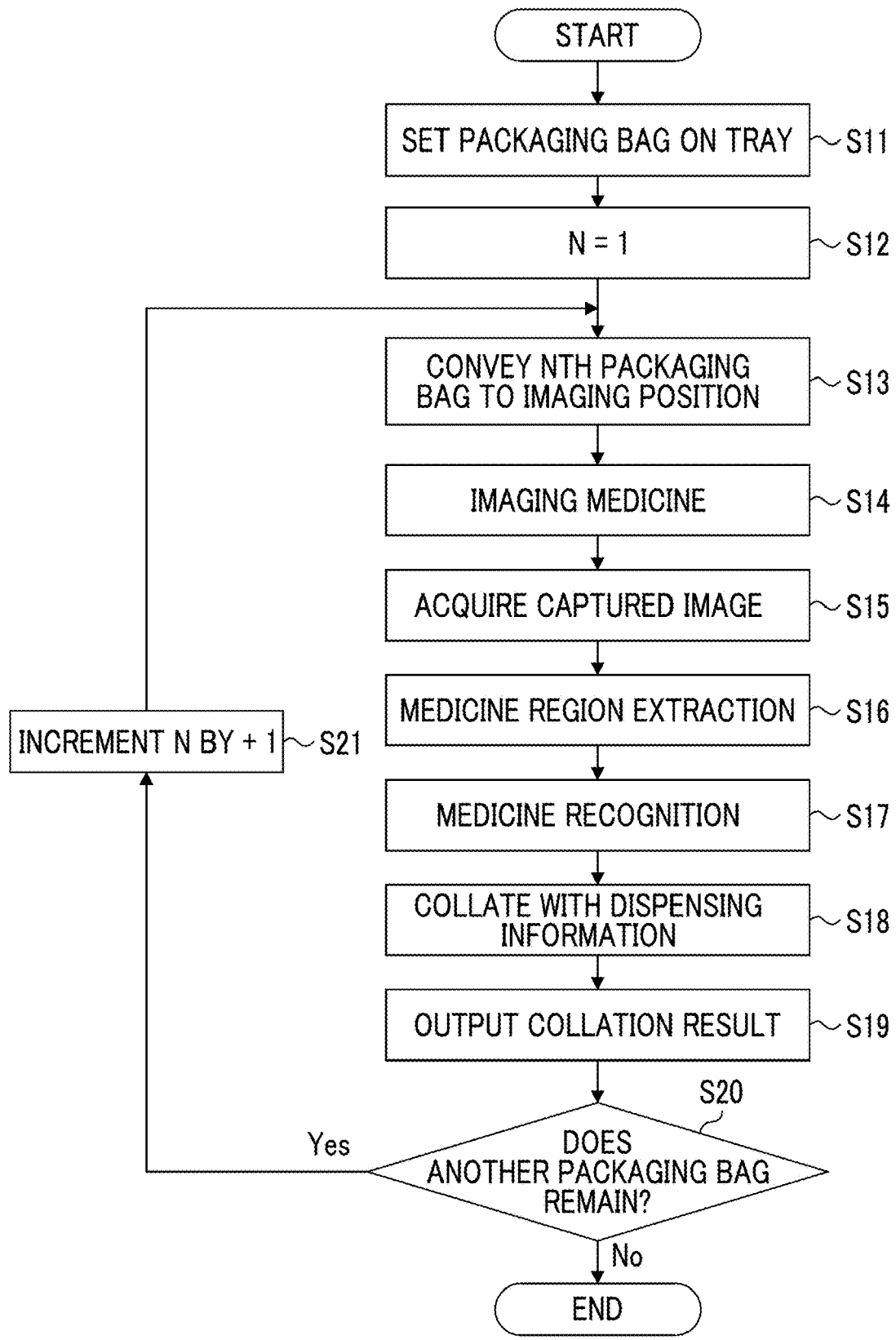
FIG. 4 is a flowchart showing a flow of audit processing by the medicine audit apparatus according to the embodiment.

FIG. 4 is a flowchart showing a flow of audit processing by the medicine audit apparatus 10 according to the embodiment.

According to the dispensing information 72 input to the receipt computer 70 in advance, the pharmacist sets the medicines 12 in the packaging apparatus, and the medicines 12 are packaged in a plurality of the packaging bags 11 in the packaging apparatus. The series of packaging bags 11 in which the medicines 12 are packaged in the packaging apparatus is set on the tray 17 of the medicine audit apparatus 10 (step S11). In a case where an audit start operation is performed by the operation unit 60, the overall control unit 62 operates each unit of the medicine audit apparatus 10 to start the recognition of the types of the medicines 12 packaged in the series of packaging bags 11 and the audit.

In step S12, the overall control unit 62 sets N=1 as a parameter N indicating a number of a packaging bag 11 to be processed.

In step S13, the conveyance control unit 32 operates the conveyance mechanism 18 to convey an Nth packaging bag 11 to an imaging position. The imaging position is a position of an inner side of the light source holding unit 24 that can be imaged by the camera 21. The tray 17 is conveyed by the conveyance mechanism 18 to set the Nth packaging bag in the light source holding unit 24.

In step S14, the imaging control unit 34 executes the imaging by the camera 21 to image the medicine 12. An imaging step in step S14 includes a setting of the illumination condition by the illumination apparatus 30 and an operation of the light emission of the illumination apparatus 30 according to the setting. The imaging by the camera 21 is performed in a state where the illumination light is irradiated by the illumination apparatus 30.

In step S15, the information processing apparatus 22 acquires the captured image from the camera 21 through the image acquisition unit 40. The captured image obtained from the camera 21 is stored in the memory 41.

In step S16, the information processing apparatus 22 performs processing of extracting the medicine region from the captured image by the edge detection unit 55.

Figure 5:
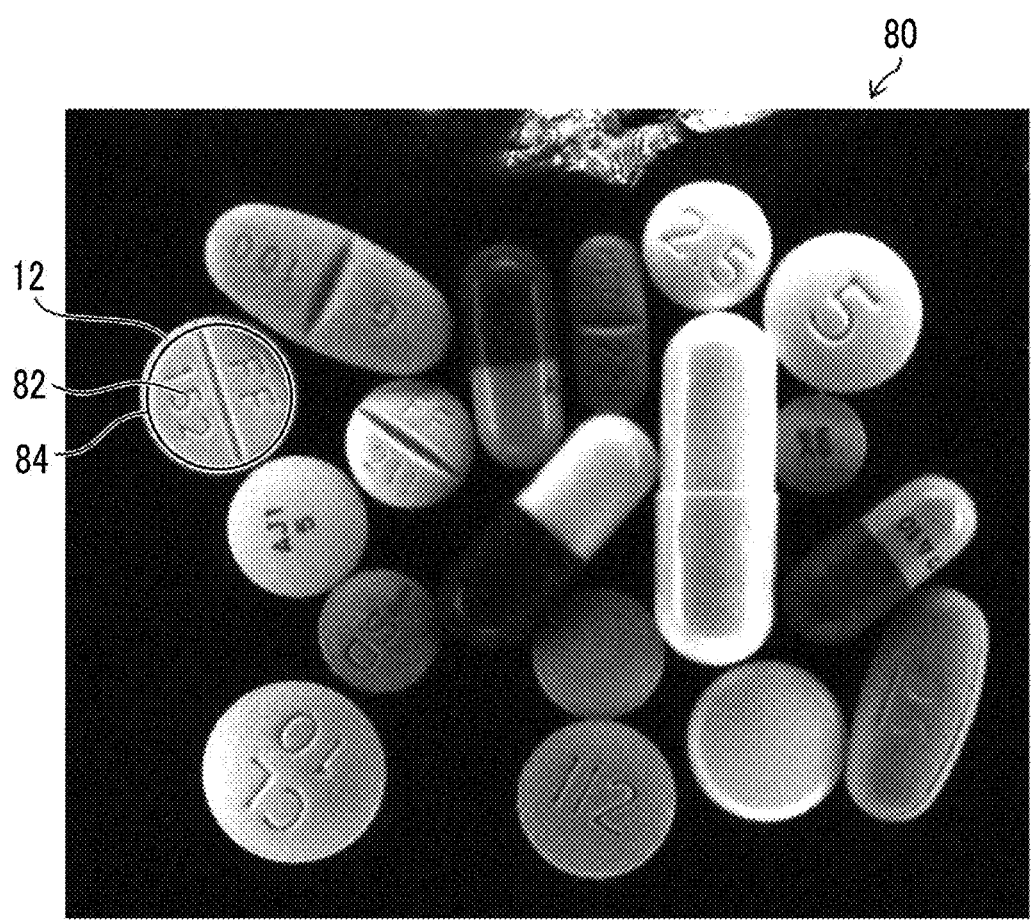
FIG. 5 is an example of a captured image obtained by imaging medicines.

FIG. 5 is an example of a captured image 80. The captured image 80 is an image obtained by imaging the one-packaging medicines for one package in which a plurality of types of the medicines 12 are accommodated in the packaging bag 11. Engraved marks 82 are assigned on the surfaces of the medicines 12. A medicine region 84 corresponding to an image portion of the medicine 12 is extracted for each of the plurality of medicines 12 included in the captured image 80. In FIG. 5, a circle is displayed for highlighting the medicine region 84.

Next, in step S17 in FIG. 4, the engraved mark recognition unit 56 of the information processing apparatus 22 performs medicine recognition processing of specifying the type of the medicine of each medicine region extracted by step S16. The engraved mark recognition unit 56 obtains the information on the engraved mark assigned on each medicine 12 recorded in the dispensing information 72 with reference to the medicine database based on the dispensing information 72. The engraved mark recognition unit 56 distinguishes the engraved mark assigned on the medicine of the medicine region extracted based on the information on the edge detected by the edge detection unit 55. The engraved mark recognition unit 56 compares the information on the engraved mark acquired based on the dispensing information 72 with the engraved mark distinguished from the captured image to recognize the engraved mark included in the captured image. It is possible to reduce incorrect recognition of the engraved mark in a case where a shape of the engraved mark included in the captured image is incomplete, for example, even in a case where distortion, missing, or the like occurs in a part of the engraved mark by comparing with the dispensing information 72 in this manner.

As described above, the engraved mark recognition unit 56 specifies the type of each medicine 12 in the Nth packaging bag 11 with reference to the medicine database based on the engraved mark respectively recognized from the captured image and outputs the medicine recognition result to the audit unit 65.

Next, in step S18, the audit unit 65 of the information processing apparatus 22 collates the type of the medicine specified by step S17 with the dispensing information 72.

In step S19, the audit unit 65 outputs the collation result to the display unit 46. The display unit 46 displays the collation result by the audit unit 65. At the case, in a case where the collation result does not match, the display unit 46 displays a type name of the medicine 12 to perform the warning to the pharmacist or the like who performs a dispensing audit. In a case where a determination result indicating that the recognition of the medicine 12 fails is input from the medicine recognition unit 54, the display unit 46 displays the determination result to perform the warning to the pharmacist or the like who performs the dispensing audit.

The recognition of the types of the medicines 12 packaged in the Nth packaging bag 11 and the audit are completed.

Next, in step S20, it is determined whether another packaging bag remains. In a case where a packaging bag 11 to which the audit is not yet processed among the series of packaging bags 11 remains, the processing proceeds to step S21, increments the value of the parameter N, sets a value of "N+1" as a new value of the parameter N of the packaging bag number, and returns to step S13.

The processing of each step from steps S13 to S20 described above is repeatedly executed. In a case where the recognition of the types of the medicines 12 and the audit are completed for the series of packaging bags 11, the determination in step S20 becomes a NO determination, and the flowchart of FIG. 4 ends.

Step S15 in FIG. 4 corresponds to one embodiment of an image acquisition step. A combination of steps S16 and S17 corresponds to one embodiment of a medicine recognition step.

[Problem of Medicine Recognition] In order to execute the audit processing described by the flowchart of FIG. 4, it is necessary to succeed the processing of extracting the medicine region 84 of each medicine 12 from the captured image (step S16), to succeed the processing of recognizing the engraved mark 82 from the extracted medicine region 84 (step S17), and to specify the type of the medicine 12.

However, in a case where the captured image is blurred or the like, there may be a case where the extraction of the medicine region and the processing of the engraved mark recognition fail. The captured image is blurred means that the sharpness of the captured image is low. In such case, even though the flowchart of FIG. 4 is implemented, it is impossible to perform the recognition of the medicine 12. Therefore, in the medicine audit apparatus 10 according to the embodiment, the functions of detecting the problem state where the medicine recognition processing by the medicine recognition unit 54 is impossible and of informing the user are mounted.

[About Case where Sharpness of Captured Image is Low and Medicine Recognition is Impossible]

Figure 6:
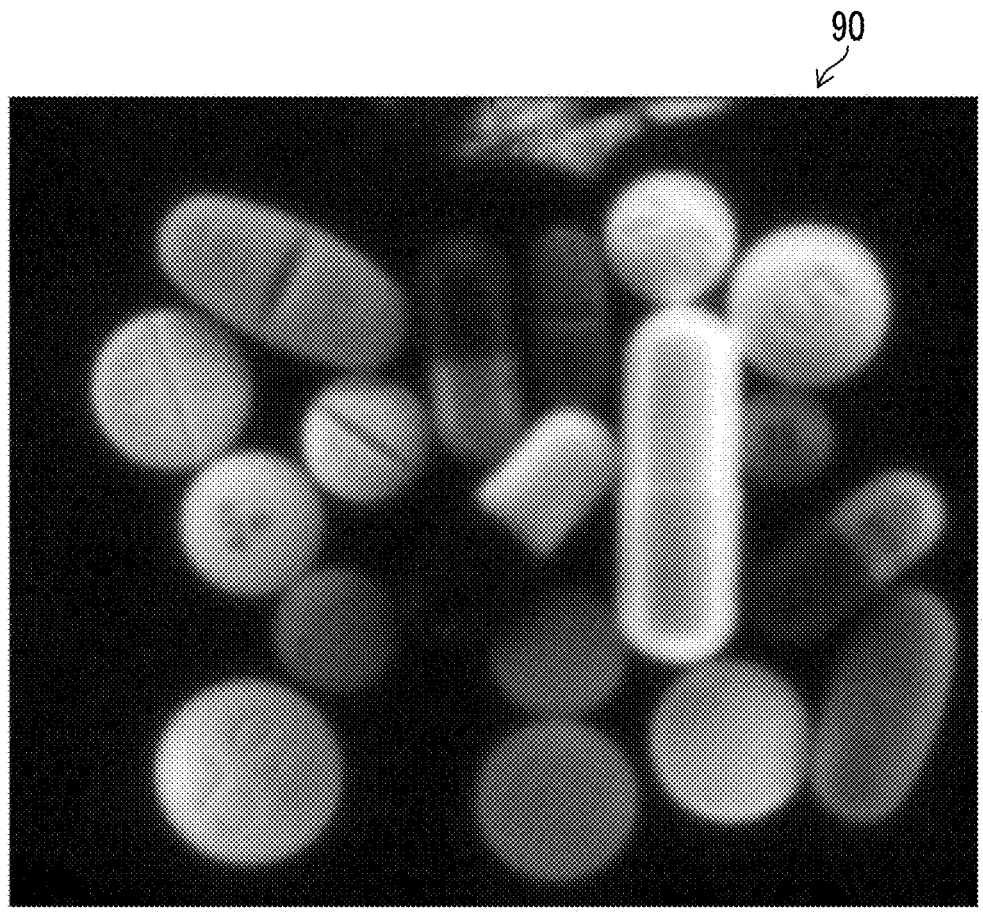
FIG. 6 is another example of a captured image obtained by imaging the medicines.

FIG. 6 is an example of a captured image 90 to be compared with FIG. 5. In FIG. 6, the sharpness is reduced compared with FIG. 5, and the image is blurred.

FIG. 6 is the example of the image in which the captured image 90 is blurred and the extraction of the medicine region by the medicine recognition unit 54, that is, the edge detection does not succeed.

Figure 7:
FIG. 7 is an example of an edge extraction image extracted by implementing processing of edge detection on the captured image shown in FIG. 5.

FIG. 7 is an edge extraction image extracted by implementing processing of the edge detection on the captured image 80 shown in FIG. 5. In FIG. 7, the edge detection is normally performed, and a normal edge detection image is obtained.

Figure 8:
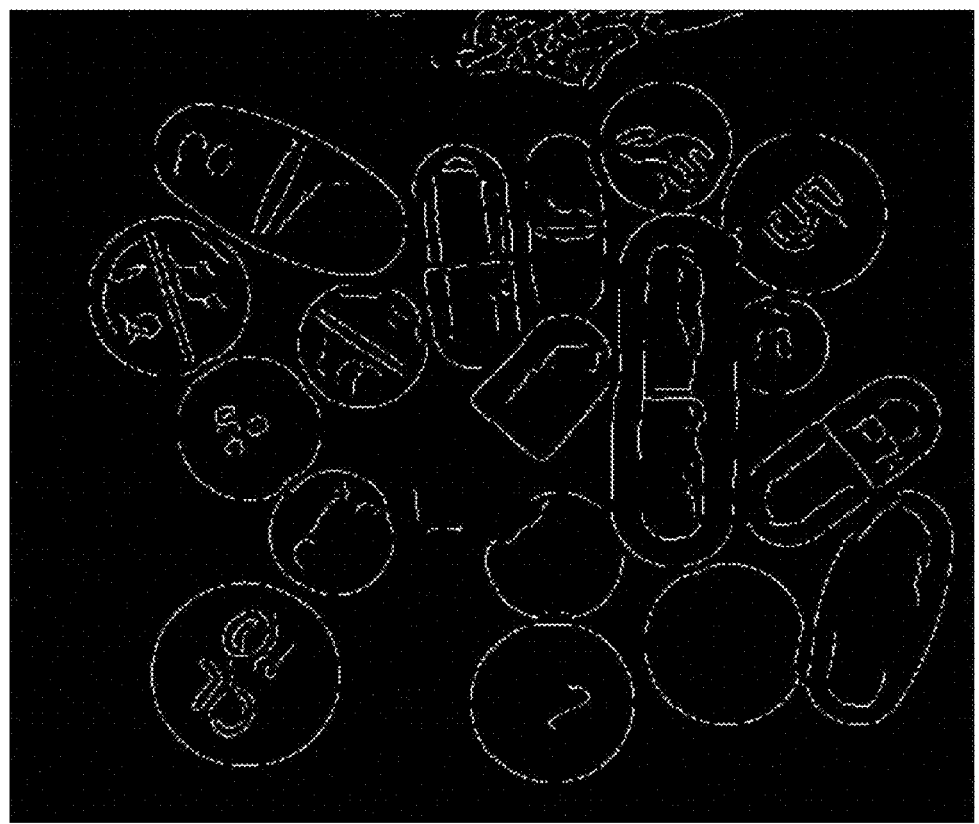
FIG. 8 is an example of an edge extraction image extracted by implementing the processing of the edge detection on the captured image shown in FIG. 6.

FIG. 8 is an edge extraction image extracted by implementing the processing of the edge detection on the captured image 90 shown in FIG. 6. In FIG. 8, the captured image 90 is blurred, and the outline of the medicine cannot be sufficiently extracted. For example, the extraction of the outline of the capsule located at the center part of FIG. 8 is insufficient.

As shown in FIG. 6, a plurality of reasons why the sharpness of the captured image is reduced are considered. For example, scattering due to dust of the tablet, scattering due to a packaging material, and the like are considered. In such case, it is necessary to inform the user that the detection of the medicine 12 is impossible.

In the embodiment, the ratio between the high-frequency component corresponding to the edge and the low-frequency component other than the edge is stored in advance in the apparatus as the threshold value using the processing of the two-dimensional fast Fourier transform, and the state where the captured image is blurred to a level at which the medicine recognition is impossible is detected depending on whether the captured image exceeds the threshold value. The processing of the two-dimensional fast Fourier transform corresponds to one embodiment of the processing of two-dimensional Fourier transform.

In the case of the embodiment, the two-dimensional fast Fourier transform image is standardized based on Parseval's theorem, and the threshold value is decided using the absolute values of the obtained spectra. Specifically, the ratio is taken between the sum of the absolute values of larger spatial frequency spectra than one [cycle/mm] and the sum of the absolute values of spatial frequency spectra equal to or less than one [cycle/mm] of the two-dimensional fast Fourier transform image of the captured image in the radial direction. Since the high-frequency component of the captured image depends on the number of medicines packaged, the same effect as standardized by the number of the medicines can be obtained.

[Specific Example of Quantitative Value]

Hereinafter, a case of using the method of Canny edge detection will be described as an example.

It is possible to use a quantitative value T defined below as the value indicating the quality of the captured image quantitatively.

$$T = S_E / S_{NE}$$

$S_E$ is the sum of the absolute values of larger spatial frequency spectra than one [cycle/mm] in the two-dimensional fast Fourier transform image of the captured image in the radial direction. $S_{NE}$ is the sum of the absolute values of the spatial frequency spectra equal to or less than one [cycle/mm] in the two-dimensional fast Fourier transform image of the captured image in the radial direction.

The threshold value for the quantitative value T is held in the apparatus in advance.

The one [cycle/mm] is the lowest spatial frequency that forms the outline of the medicine. The $S_E$ is a value reflecting an outline part of the medicine, and the $S_{NE}$ is a value reflecting a non-outline part of the medicine.

In the equation defining the quantitative value T, the ratio of the spectra sum is taken for standardizing the quantitative value by the number of the medicines falling within the field of view range. An average value of the image is not used for the spectra sum.

[Calculation Example of Threshold Value]

The quantitative value T is one index indicating the blurriness of the captured image and can be understood as a blur quantitative value or a sharpness quantitative value. In order to decide the threshold value of the quantitative value T defined above, the captured image imaged under an appropriate imaging condition where the medicine recognition is possible is blurred by the simulation to create the image with reduced sharpness. The blur added by the simulation is defined by an equation of Exp (−0.020×π×C×f).

The function of Exp (x) represents "e" that is the base number of natural logarithm to an xth power. The C is a predetermined parameter. The f is the spatial frequency [cycle/mm].

It is confirmed whether the outlines of the tablet and the capsule appear by the processing of the edge detection by the method of Canny edge detection while the value of the predetermined parameter C is changed, and the quantitative value T under each condition is calculated.

FIG. 9 is a table summarizing the predetermined values of the parameter C, propriety results of outline extractions of the medicines, and values of the quantitative value T calculated under each condition. "A" in an evaluation of the medicine outline extraction propriety indicates that the extraction of the outline of the medicine succeeds. "D" indicates that the extraction of the outline of the medicine fails.

In the case of using the Canny edge detection, it is understood that the threshold value may be set to "1.19" from the table of FIG. 9. The threshold value decided as described above is stored in the threshold value storage unit 52 of FIG. 3.

The threshold value may be provided for each of the edge detection methods such as a method of using a Sobel filter or a method of using a Laplacian filter in addition to the Canny method.

The quantitative value T is calculated by the quantitative value calculation unit 50 for each captured image for the threshold value decided as described above, the medicine recognition is determined to be impossible in a case where the quantitative value T calculated for each captured image is less than the threshold value, and the warning of informing the user of the state where the medicine recognition is impossible is output. A method of outputting the warning by the warning output unit 58 may be an alert, a screen display on the display unit 46, or a combination thereof. It is preferable that the warning includes information that informs the user of a reason why the medicine recognition is impossible. For example, the warning information displayed in the display unit 46 of the example includes information that informs the user that the medicine recognition is impossible due to the low sharpness of the captured image.

The quantitative value T is an example of the quantitative value for quantifying the quality of the captured image related to success or failure of the edge detection by the edge detection unit 55. The threshold value decided from the result of the simulation shown in FIG. 9 is an example of the threshold value of the quantitative value that is the determination criterion whether the edge detection by the edge detection unit 55 is possible.

The determination whether the medicine recognition by the medicine recognition unit 54 is possible performed by the comparison determination unit 51 based on the quantitative value T corresponds to the determination whether the edge detection by the edge detection unit 55 is possible. In a case where it is determined that the edge detection of the edge detection unit 55 by the comparison determination unit 51 is impossible, the warning output unit 58 issues the warning indicating the fact.

[Medicine Audit Method According to Embodiment]

Figure 10:
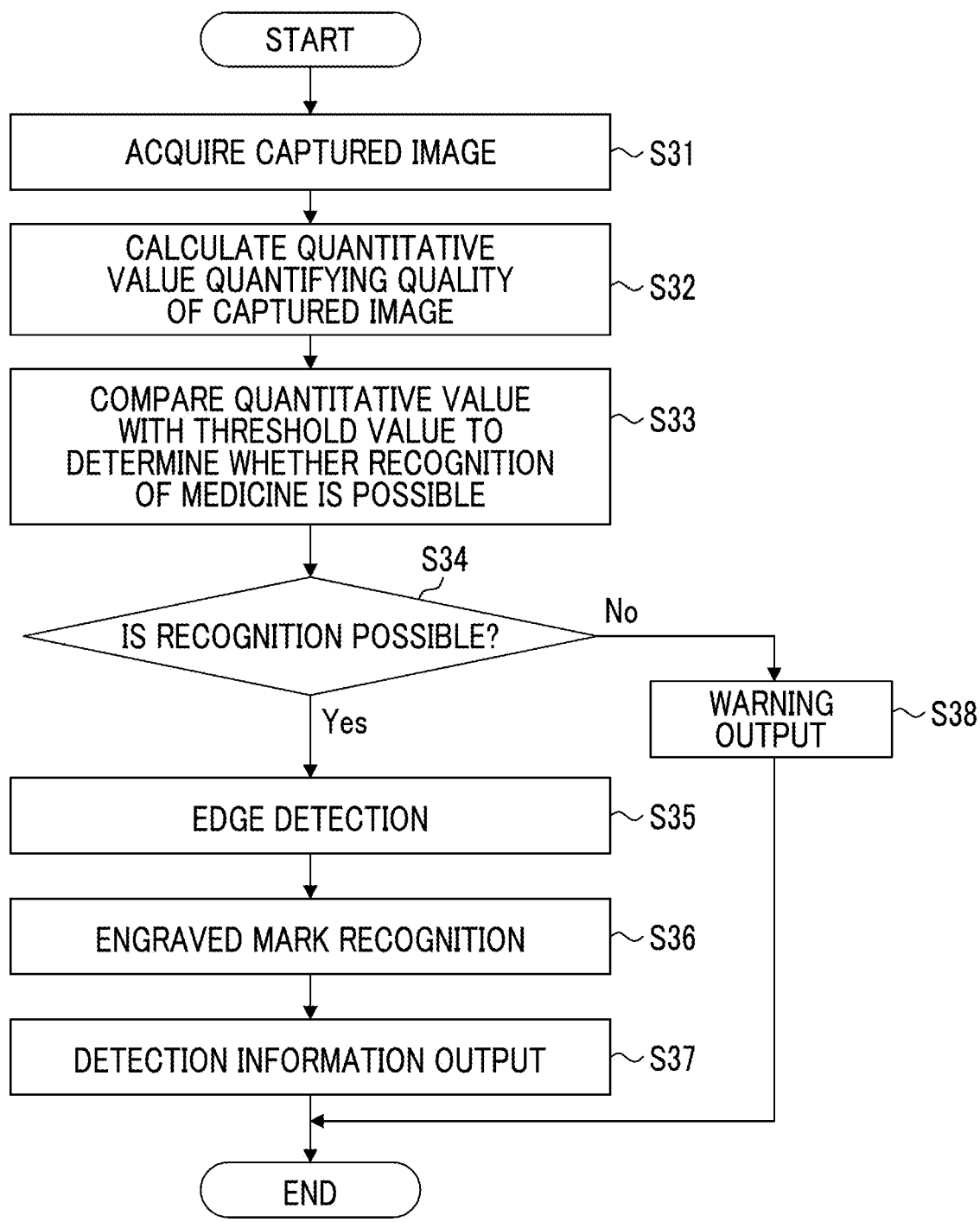
FIG. 10 is a flowchart showing a flow of processing of an information processing apparatus in the medicine audit apparatus according to the embodiment.

FIG. 10 is a flowchart showing a flow of processing of the information processing apparatus 22 in the medicine audit apparatus 10 according to the embodiment. The medicine audit method according to the embodiment will be described using FIG. 10.

In step S31, the information processing apparatus 22 acquires the captured image through the image acquisition unit 40. Step S31 corresponds to step S15 in the flowchart of FIG. 4.

Next, in step S32 of FIG. 10, the quantitative value calculation unit 50 calculates the quantitative value for quantifying the quality of the captured image. The quantitative value calculation unit 50 calculates, for example, the quantitative value T quantifying the sharpness of the captured image.

In step S33, the comparison determination unit 51 compares the quantitative value obtained in step S32 with the threshold value stored in the threshold value storage unit 52 in advance to determine whether the recognition of the medicine is possible.

In step S34, in a case where the comparison determination unit 51 determines that the medicine recognition is possible, the processing proceeds to step S35.

In step S35, the edge detection unit 55 performs the edge detection processing of the captured image. The extraction of the medicine region is performed based on a processing result of the edge detection processing. An edge detection step in step S35 is a step corresponding to a medicine region extraction step described as step S16 of FIG. 4.

After step S35 of FIG. 10, in step S36, the engraved mark recognition unit 56 performs processing of recognizing the engraved mark in each medicine region and specifying the type of the medicine. An engraved mark recognition step in step S36 is a step corresponding to the medicine recognition step described as step S17 of FIG. 4.

In a case where the type of the medicine is specified in step S36 of FIG. 10, in step S37, the medicine recognition unit 54 outputs detection information that is information of the specified medicine. Step S37 may be understood as a step of providing information from the medicine recognition unit 54 to the audit unit 65 or may be understood as a step of outputting the information on the medicine recognized by the medicine recognition unit 54 to the display unit 46. Alternatively, step S37 may be understood as a step of outputting an audit result by the audit unit 65 to the display unit 46.

In step S34, in a case where the comparison determination unit 51 determines that the medicine recognition is impossible, the processing proceeds to step S38. In step S38, the warning output unit 58 outputs the warning of informing the state where the medicine recognition is impossible.

The flowchart shown in FIG. 10 is implemented for each captured image to be input.

Step S31 in FIG. 10 corresponds to one embodiment of the image acquisition step. Step S32 corresponds to one embodiment of a quantitative value calculation step. Step S33 corresponds to one embodiment of a comparison determination step. A combination of steps S35 and S36 corresponds to one embodiment of the medicine recognition step. Step S38 corresponds to one embodiment of a warning output step.

According to the embodiment, it is possible to evaluate the quality of the captured image by calculating the quantitative value T from the captured image obtained by imaging the medicine and to determine whether the captured image is in the state where the medicine recognition is impossible by comparing the quantitative value T with the threshold value. In a case where it is detected the state where the medicine recognition is impossible, it is possible to urge the user to pay attention. Accordingly, it is possible to perform the efficient medicine audit.

[About Program Causing Computer to Function as Medicine Audit Apparatus]

It is possible to record a program for causing a computer to realize a medicine audit function of the information processing apparatus 22 described in the above embodiment in a non-transitory information storage medium as a tangible object that is a compact disc read-only memory (CD-ROM), a magnetic disk, or another computer-readable medium and to provide the program through the information storage medium. It is also possible to provide a program signal as a download service using a communication network such as the Internet instead of the embodiment in which the program is stored and provided in such information storage medium.

It is also possible to realize a part or all of the medicine audit function of the information processing apparatus 22 described in the above embodiment by an application server or cloud computing and to perform a service in which a processing function is provided through a network.

Modification Example 1

In the embodiment described above, a system embodiment of the medicine audit apparatus 10 comprising the conveyance mechanism 18 of the tray 17, the illumination apparatus 30, the camera 21, and the information processing apparatus 22 is described. However, it is possible to grasp function portions of the image acquisition unit 40, the image processing unit 42, and the warning output unit 58 in the information processing apparatus 22 as one embodiment of "medicine audit apparatus" regardless of presence or absence of the conveyance mechanism 18, the illumination apparatus 30, and the camera 21. The processing functions of the information processing apparatus 22 are not limited to the embodiment realized by one computer, and it is also possible to employ an embodiment of realizing the processing functions of the information processing apparatus 22 by sharing the functions of the processing by a plurality of computers and combining the plurality of computers.

For example, a computer that shares the functions of the conveyance control unit 32, the illumination control unit 33, and the imaging control unit 34, and a computer that shares the functions of the image acquisition unit 40, the memory 41, the image processing unit 42, the display control unit, the warning output unit 58, the operation unit 60, the overall control unit 62, the medicine database storage unit 63, the dispensing information acquisition unit 64, and the audit unit 65 can be configured by separate computers. For example, a part or all of the functions of the information processing apparatus 22 may be mounted on the receipt computer 70.

Modification Example 2

The medicine database storage unit 63 may be an external storage apparatus connected to the information processing apparatus 22. For example, the medicine database may be stored in a storage apparatus of a computer owned by a dispensing pharmacy. The medicine database may be held in the receipt computer 70. The medicine database may be held in another computer not shown and may employ an embodiment in which the information processing apparatus 22 acquires information from the medicine database via the network. The network may be a local area network, a wide area network, or a combination thereof.

Modification Example 3

The captured image to be calculated the quantitative value by the quantitative value calculation unit 50 is not limited to the image data 28 output from the camera 21 and may be the image data generated based on the image data 28 output from the camera 21. For example, an image obtained by implementing the processing such as the noise removal processing, the color conversion processing, gradation transformation processing, or a combination thereof on the image data 28 output from the camera 21 is included in the concept of the captured image. An image obtained by processing the image data 28 output from the camera 21 is also included in the concept of the captured image, and a composite image obtained by compositing a plurality of captured images obtained by implementing a plurality of times of imaging is also included in the concept of the captured image.

Modification Example 4

In a case of an embodiment comprising a second camera that images the medicine from a second surface side that is the lower surface side of the packaging bag 11 in addition to the camera 21 as a first camera that images the medicine from a first surface side that is the upper surface side of the packaging bag 11 placed on the tray 17, it is possible to employ the processing by the flowchart described in FIG. 10 on each captured image of the captured image obtained from the first camera and the captured image obtained from the second camera.

The audit unit 65 may collate the recognition result of the medicine recognition processing based on the captured image obtained from the first camera and the recognition result of the medicine recognition processing based on the captured image obtained from the second camera together with the dispensing information 72.

Modification Example 5

The example of defining the quantitative value T as the example of the quantitative value for quantifying the quality of the captured image is described. However, the deciding method of the quantitative value is not limited to the example, and it is possible to define various indexes.

Modification Example 6

In the embodiment described above, the example of imaging the plurality of medicines accommodated in the packaging bag 11 according to a one-packaging dispensing is described. However, a system embodiment of recognizing the medicines before the medicines are accommodated in the packaging bag 11 may also employ the same configuration as the information processing apparatus 22 according to the embodiment described above. For example, an embodiment may be employed in which an inspection pod for imaging the medicines is provided in the middle of a medicine passage leading to a hopper that puts the medicines for one package into the packaging bag 11 in the packaging apparatus, and the illumination apparatus and the camera are disposed on the inspection pod.

In the embodiment described above, the example of the medicine audit according to the one-packaging dispensing is shown. However, the medicine audit function by the information processing apparatus 22 is not limited to the medicine audit according to the one-packaging dispensing, and it is possible to widely employ to the medicine audit that performs the medicine recognition processing. For example, a system embodiment of recognizing the type of the medicine from the captured image obtained by imaging the medicine by the camera in a state of a press through pack (PTP) sheet that is a dispensing package unit may also employ the same configuration as the information processing apparatus 22.

The embodiment of the present invention and the modification examples are described. However, the present invention is not limited to the embodiment and the modification examples, and various modifications are possible within a range of not departing from the gist of the present invention.

EXPLANATION OF REFERENCES

10: medicine audit apparatus
11: packaging bag
12: medicine
17: tray
18: conveyance mechanism
19: projector
20: backlight
21: camera
22: information processing apparatus
24: light source holding unit
24*a*: opening window
25: point light source
28: image data
30: illumination apparatus
32: conveyance control unit
33: illumination control unit
34: imaging control unit
40: image acquisition unit
41: memory
42: image processing unit
44: display control unit
46: display unit
50: quantitative value calculation unit
51: comparison determination unit
52: threshold value storage unit
54: medicine recognition unit
55: edge detection unit
56: engraved mark recognition unit
58: warning output unit
60: operation unit
62: overall control unit
63: medicine database storage unit
64: dispensing information acquisition unit
65: audit unit
70: receipt computer
72: dispensing information
80: captured image
82: engraved mark
84: medicine region
90: captured image
S11 to S21: steps of medicine audit processing
S31 to S38: steps of medicine audit method according to the embodiment

What is claimed is:
1. A medicine audit apparatus comprising:
an image acquisition unit that acquires a captured image of a medicine;
a medicine recognition unit that specifies a type of the medicine by recognizing the medicine from the captured image;
a quantitative value calculation unit that calculates a quantitative value for quantifying a quality of the captured image;

a storage unit that stores a threshold value;
a comparison determination unit that compares the quantitative value calculated by the quantitative value calculation unit with the threshold value to determine whether the recognition of the medicine by the medicine recognition unit is possible; and
a warning output unit that issues a warning in a case where the medicine recognition of the medicine recognition unit is determined to be impossible by the comparison determination unit,
wherein the medicine recognition unit includes:
an edge detection unit that detects an edge of the medicine from the captured image; and
an engraved mark recognition unit that recognizes an engraved mark assigned on the medicine extracted based on information on the edge detected by the edge detection unit from the captured image,
wherein the quantitative value quantifies the quality of the captured image related to edges of the captured image, and
wherein the threshold value is a determination criterion whether the edge detection by the edge detection unit is possible,
wherein the determination whether the recognition of the medicine by the medicine recognition unit is possible, which is performed by the comparison determination unit, is a determination whether the edge detection by the edge detection unit is possible, and
wherein the quantitative value calculation unit calculates the quantitative value using a ratio between a sum of absolute values of spatial frequency spectra of higher frequencies than one cycle/mm and a sum of absolute values of spatial frequency spectra of lower frequencies than one cycle/mm in the spatial frequency spectra obtained by performing processing of two-dimensional Fourier transform on the captured image in a radial direction.

2. The medicine audit apparatus according to claim 1, wherein the quality of the captured image includes sharpness of the captured image.

3. The medicine audit apparatus according to claim 1, wherein in a case where the quantitative value calculated by the quantitative value calculation unit is less than the threshold value, the warning output unit outputs the warning.

4. The medicine audit apparatus according to claim 1, wherein the warning output unit includes a display unit that displays information on the warning.

5. The medicine audit apparatus according to claim 1, further comprising:
a camera that images the medicine,
wherein the image acquisition unit acquires a captured image imaged by the camera.

6. The medicine audit apparatus according to claim 1, wherein the captured image is an image obtained by imaging one-packaging medicines for one package in which a plurality of types of medicines are accommodated in a packaging bag.

7. A medicine audit method comprising:
an image acquisition step of acquiring a captured image of a medicine;
a medicine recognition step of specifying a type of the medicine by recognizing the medicine from the captured image;
a quantitative value calculation step of calculating a quantitative value for quantifying a quality of the captured image;
a comparison determination step of comparing a threshold value with the quantitative value calculated by the quantitative value calculation step to determine whether the recognition of the medicine by the medicine recognition step is possible; and
a warning output step of issuing a warning in a case where the medicine recognition of the medicine recognition step is determined to be impossible in the comparison determination step,
wherein the medicine recognition step includes:
an edge detection step of detecting an edge of the medicine from the captured image; and
an engraved mark recognition step of recognizing an engraved mark assigned on the medicine extracted based on information on the edge detected by the edge detection step from the captured image,
wherein the quantitative value is a quantitative value that quantifies the quality of the captured image related to edges of the captured image, and
wherein the threshold value is a determination criterion whether the edge detection by the edge detection step is possible,
wherein the determination whether the recognition of the medicine by the medicine recognition step is possible, which is performed by the comparison determination step, is a determination whether the edge detection by the edge detection step is possible, and
wherein the quantitative value calculation step calculates the quantitative value using a ratio between a sum of absolute values of spatial frequency spectra of higher frequencies than one cycle/mm and a sum of absolute values of spatial frequency spectra of lower frequencies than one cycle/mm in the spatial frequency spectra obtained by performing processing of two-dimensional Fourier transform on the captured image in a radial direction.

8. A recording medium that is a non-transitory computer-readable recording medium and records a program, in a case where the program stored in the recording medium is read by the computer, the program causing the computer to execute:
an image acquisition step of acquiring a captured image of a medicine;
a medicine recognition step of specifying a type of the medicine by recognizing the medicine from the captured image;
a quantitative value calculation step of calculating a quantitative value for quantifying a quality of the captured image;
a comparison determination step of comparing a threshold value with the quantitative value calculated by the quantitative value calculation step to determine whether the recognition of the medicine by the medicine recognition step is possible; and
a warning output step of issuing a warning in a case where the medicine recognition of the medicine recognition step is determined to be impossible in the comparison determination step,
wherein the medicine recognition step includes:
an edge detection step of detecting an edge of the medicine from the captured image; and
an engraved mark recognition step of recognizing an engraved mark assigned on the medicine extracted based on information on the edge detected by the edge detection step from the captured image,
wherein the quantitative value is a quantitative value for quantifying the quality of the captured image related to edges of the captured image, and wherein the threshold value is a determination criterion whether the edge detection by the edge detection unit is possible, wherein the determination whether the recognition of the medicine by the medicine recognition step is possible, which is performed by the comparison determination step, is a determination whether the edge detection by the edge detection step is possible, and wherein the quantitative value calculation step calculates the quantitative value using a ratio between a sum of absolute values of spatial frequency spectra of higher frequencies than one cycle/mm and a sum of absolute values of spatial frequency spectra of lower frequencies than one cycle/mm in the spatial frequency spectra obtained by performing processing of two-dimensional Fourier transform on the captured image in a radial direction.

* * * * *